United States Patent [19]

Gsell et al.

[11] Patent Number: 4,798,912
[45] Date of Patent: Jan. 17, 1989

[54] SUBSTITUTED PHENOXYBENZYL-(DIHALODIMETHYL-CYCLOPROPYL-METHYL)ETHERS

[75] Inventors: Laurenz Gsell, Basel; Peter Ackermann, Pfeffingen, both of Switzerland

[73] Assignee: Ciba-Geigy Corporation, Ardsley, N.Y.

[21] Appl. No.: 118,816

[22] Filed: Nov. 9, 1987

[30] Foreign Application Priority Data

Nov. 19, 1986 [CH] Switzerland ............ 4619/86
Oct. 1, 1987 [CH] Switzerland ............ 3822/87

[51] Int. Cl.⁴ .................................. C07C 43/225
[52] U.S. Cl. ........................................ 568/637
[58] Field of Search ............. 568/637, 588, 639, 638

[56] References Cited

U.S. PATENT DOCUMENTS 4,238,504 12/1980 Drakek et al. .............. 568/637
4,381,412 4/1983 Fuchs et al. .............. 568/637

*Primary Examiner*—Werren B. Lone
*Attorney, Agent, or Firm*—Kevin T. Mansfield; Edward McC. Roberts

[57] ABSTRACT

Novel substituted phenoxybenzyldihalodimethyl-cyclopropylmethyl ethers of the formula

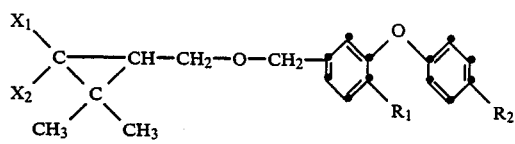

in which $X_1$ and $X_2$ each independently of the other represents fluorine, chlorine or bromine;
$R_1$ represents hydrogen or flourine; and
$R_2$ represents hydrogen, fluorine, chlorine, bromine, methyl, trifluoromethyl or methoxy, and, if $X_1$ and $X_2$ have different meanings, the optical isomers of the compound of the formula I; processes for the manufacture of those compounds, and compositions containing them for use in pest control, especially for the control of insects, especially the larval stages thereof, that attack plants and animals, and of phytopathogenic fungi. The novel compounds exhibit good activity especially against insects that damage plants in rice crops.

13 Claims, No Drawings

SUBSTITUTED PHENOXYBENZYL-(DIHALODIMETHYLCYCLOPROPYL-METHYL)ETHERS

The present invention relates to novel substituted (3-phenoxybenzyl)-(2,2-dihalo-3,3-dimethylcyclopropylmethyl) ethers and their optical isomers, to processes for the manufacture of the novel compounds and to their use in pest control.

The novel ethers according to the invention have the formula I

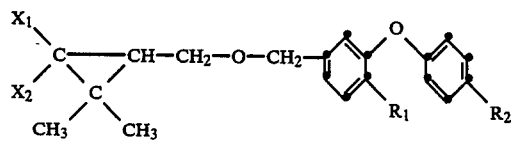

in which
$X_1$ and $X_2$ each independently of the other represents fluorine, chlorine or bromine;
$R_1$ represents hydrogen or fluorine; and
$R_2$ represents hydrogen, fluorine, chlorine, bromine, methyl, trifluoromethyl or methoxy.

The present invention also includes optical isomers of compounds according to formula I.

In view of their biological action, attention is drawn to compounds of the formula I in which
$X_1$ and $X_2$ represent chlorine;
$R_1$ represents hydrogen or fluorine; and
$R_2$ represents hydrogen, fluorine, chlorine or bromine.

The compounds of the formula I are manufactured in a manner known per se, as follows:

(a) a compound of the formula II or IIa

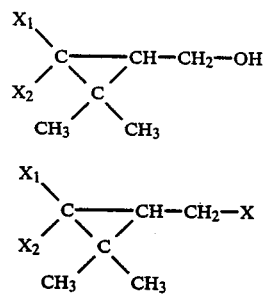

is reacted with a compound of the formula III or IIIa

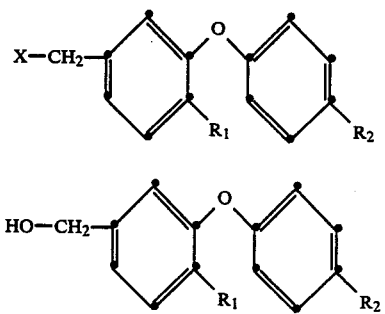

or (b) a compound of the formula IV

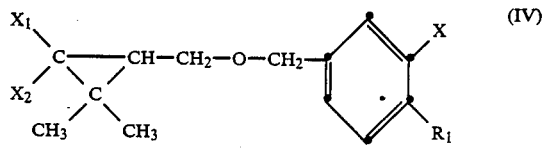

is reacted with a compound of the formula V

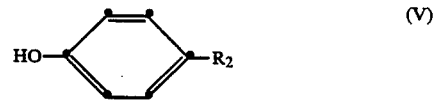

in which formulae $X_1$, $X_2$, $R_1$ and $R_2$ have the meanings given above and X represents a halogen atom, preferably bromine or iodine, and, in the case of the compounds of the formulae IIa and III, also represents the p-toluenesulphonate group.

The above processes are effected at a reaction temperature of from $-10°$ to $120°$ C., generally of from 20 to 80° C., at normal or elevated pressure and preferably in an inert solvent or diluent. Suitable solvents and diluents are, for example, ethers and ethereal compounds, such as diethyl ether, dipropyl ether, dioxan, dimethoxyethane and tetrahydrofuran; amides, such as N,N-dialkylated carboxylic acid amides; aliphatic, aromatic and halogenated hydrocarbons, especially benzene, toluene, xylenes, chloroform and chlorobenzene; nitriles, such as acetonitrile; dimethyl sulphoxide and ketones, such as acetone and methyl ketone, and also hexane. The etherification that takes place in process (a) is advantageously carried out in the presence of bases, such as alkali metal hydroxides and alkali metal carbonates, but especially alkali metal hydrides, for example sodium hydride. The etherification that takes place in process (b) to form the phenyl ether is carried out either under the customary conditions of Ullmann condensation, or the variants thereof, or in accordance with process (a).

The starting materials of the formulae II, IIa, III, IIIa and V are known or—if they are novel—can be manufactured analogously to known methods. For example, the manufacture of the substituted cyclopropylmethanol of the formula II is described in "Tetrahedron Letters" 34, 3331–3335; the manufacture of that type of compound is also mentioned in Synthesis 1973, 112, and Helv. Chim. Acta 58, 2595 (1975). The phenoxybenzyl derivatives of the type of formulae III and IIIa and their manufacture are known, for example, from EP Patent Application No. 0 125 204, GB Patent Application No. 2 085 006 and DE-OS No. 2709355. Some of the cyclopropylmethylbenzyl ethers of the formula IV are known; they can be manufactured by reaction of the dihalodimethylcyclopropylmethanol of the formula II with a suitably substituted benzyl derivative of the formula VI

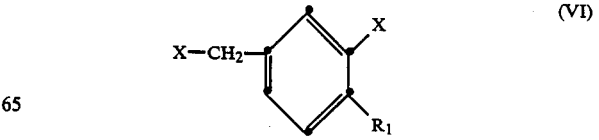

in which X and $R_1$ have the meanings given above.

Substituted dihalodimethylcyclopropylmethylalkyl ethers are already known from EP Patent Specification No. 120 238 as microbicides. In contrast to the substituted diethers according to the invention, however, those compounds have a monoether structure. In addition, U.S. Patent Specification No. 4 542 243 describes a process for the manufacture of 3-phenoxybenzyl-2-(4-alkoxyphenyl)-2-methylpropyl ethers, which differ structurally from the compounds of the formula I according to the invention especially by the absence of the cyclopropylmethyl grouping.

In contrast, it has now been found that the novel compounds of the formula I according to the invention exhibit excellent activity as pesticides while being well tolerated by plants and having low toxicity towards warm-blooded animals. They are suitable especially for controlling pests that attack plants and animals. In this connection it should be pointed out that the compounds according to the invention have very low toxicity towards fish, which is an important factor for use in rice crops.

The compounds of the formulae I are suitable especially for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also representatives of the order Acarina.

The good pesticidal action of the compounds according to the invention corresponds to a mortality of at least from 50 to 60% of the mentioned pests.

In addition to their action against mosquitos and flies, such as, for example, *Aedes aegypti* and *Musca domestica*, compounds of the formula I can also be used for controlling feeding and sucking insects that damage plants in ornamental crops and crops of useful plants, especially in rice crops (for example, against *Nilaparvata lugens* and *Nephotettix cincticeps*) and in cereal, cotton, fruit and vegetable crops (for example, against *Laspeyresia pomonella, Leptinotarsa decemlineata, Epilachna varivestis, Spodoptera littoralis* and *Heliothis virescens*). The compounds of the formula I are also distinguished by good action against the larval stages of insects and against nymphs, especially of feeding insect pests. The compounds of the formula I can also be used with great success against cicadas that damage plants, especially in rice crops.

The compounds are also suitable for controlling ectoparasites, for example *Lucilia sericata*, and ticks on pets and useful animals, for example by treatment of the animal, its shelter and the pasture.

It has further been found that compounds of the formula I have a biocidal spectrum against phytopathogenic microorganisms, especially against fungi, that is very advantageous for practical requirements. They have very advantageous curative, systemic and, especially, preventive properties and are used for protecting many crop plants. By means of the active ingredients of the formula I it is possible to check or destroy the pests that occur on plants or parts of plants (fruit, flowers, foliage, stalks, tubers and roots) of various useful crops, with the protection against phytopathogenic microorganisms continuing for parts of the plants that grow subsequently. As fungicides, the active ingredients of the formula I are effective, for example, against phytopathogenic fungi of the following classes: *Fungi imperfecti* (for example, Botrytis, Helminthosporium, Fusarium, Septoria, Cercospora and Alternaria); Basidiomycetes (for example, the genera Hemileia, Rhizoctonia, Puccinia); they are effective especially against the class of Ascomycetes (for example, Venturia, Podosphaera, Erysiphe, Monilinia, Uncinula). They may also be used as dressing agents for the treatment of propagating material (fruit, tubers, seeds) and plant seedlings in order to protect them against fungal infections and against phytopathogenic fungi that occur in the soil.

The invention relates also to compositions that contain compounds of the formula I as active ingredient component, especially plant-protecting compositions, and also to their use in farming and related fields.

Examples of target crops for the fungicidal, plant-protecting use in the context of this invention are the following plant types: cereals (wheat, barley, rye, oats, rice, corn, sorghum and related species); beet crops (sugar beet and turnips); pome fruit, stone fruit and soft fruit (apples, pears, plums, peaches, almonds, cherries, strawberries, raspberries and blackberries); legumes (beans, lentils, peas, soybeans); oil-yielding crops (rape, mustard, poppy, olives, sunflowers, coconut, castor bean, cocoa, groundnuts); Cucurbitaceae (pumpkin, cucumbers, melons); fibre plants (cotton, flax, hemp, jute); citrus fruits (oranges, lemons, grapefruit, mandarins); types of vegetable (spinach, lettuce, asparagus, cabbage types, carrots, onions, tomatoes, potatoes, red pepper); lauraceous trees (avocado, cinnamon, camphor) or plants such as tobacco, nuts, coffee, sugar cane, tea, pepper, vines, hops, banana and natural rubber plants and ornamental plants (Compositae). The compounds of the formula I, as fungicides, are effective especially in rice crops, especially against *Piricularia oryzae*.

The action of the compounds according to the invention or of the compositions containing them can be broadened considerably and adapted to given conditions by the addition of other pesticides. Suitable insecticidal and/or acaricidal additives are, for example, representatives of the following classes of active ingredient: organic phosphorus compounds, nitrophenols and derivatives thereof, formamidines, ureas, carbamates, pyrethroids, chlorinated hydrocarbons and *Bacillus thuringiensis* preparations.

The compounds of the formula I are used in unmodified form or, preferably, together with the adjuvants customary in the art of formulation and they are therefore processed in known manner, for example, into emulsifiable concentrates, directly sprayable or dilutable solutions, dilute emulsions, wettable powders, soluble powders, dusts, granulates, and encapsulations in, for example, polymeric substances. As with the compositions, the methods of application, such as spraying, atomising, dusting, scattering and pouring, are chosen in accordance with the intended objectives and the prevailing circumstances.

The formulations, i.e. the compositions or preparations containing the active ingredient or combinations of those active ingredients with other insecticides or acaricides, and, where appropriate, a solid or liquid adjuvant, are manufactured in known manner, for example by intimately mixing and/or grinding the active ingredients with extenders, such as, for example, solvents, solid carriers and, where appropriate, surface-active compounds (surfactants).

Suitable solvents are: aromatic hydrocarbons, preferably the fractions $C_8$ to $C_{12}$, such as, for example, xylene mixtures or substituted naphthalenes, phthalic acid esters, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, and also optionally epoxidised vegetable oils, such as epoxidised coconut oil or soybean oil, or water.

The solid carriers used, for example for dusts and dispersible powders, are generally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, such as, for example, pumice, broken brick, sepiolite or bentonite, and suitable nonsorbent carriers are, for example, calcite or sand. In addition, it is possible to use a large number of granulated materials of inorganic or organic nature, such as, especially, dolomite or pulverised plant residues.

Depending on the nature of the active ingredient of the formula I to be formulated or of the combinations of those active ingredients with other insecticides or acaricides, there are suitable as surface-active compounds nonionic, cationic and/or anionic surfactants having good emulsifying, dispersing and wetting properties. The term "surfactants" should also be understood as meaning mixtures of surfactants.

Suitable anionic surfactants may be both so-called water-soluble soaps and water-soluble synthetic surface-active compounds.

Suitable soaps are the alkali metal salts, alkaline earth metal salts and unsubstituted or substituted ammonium salts of higher fatty acids ($C_{10}$–$C_{22}$), such as, for example, the sodium or potassium salts of oleic or stearic acid, or of natural fatty acid mixtures, which can be obtained, for example, from coconut or tallow oil. As surfactants there should also be mentioned fatty acid methyltaurine salts and modified and unmodified phospholipids.

So-called synthetic surfactants are, however, more often used, especially fatty sulphonates, fatty sulphates, sulphonated benzimidazole derivatives or alkylarylsulphonated.

The fatty sulphonates and fatty sulphates are generally in the form of alkali metal salts, alkaline earth metal salts or unsubstituted or substituted ammonium salts and generally have an alkyl radical having from 8 to 22 carbon atoms, alkyl also including the alkyl moiety of acyl radicals, for example the sodium or calcium salt of lignosulphonic acid, of dodecylsulphuric acid ester or of a fatty alcohol sulphate mixture produced from natural fatty acids. These also include the salts of sulphuric acid esters and sulphonic acids of fatty alcohol/ethylene oxide adducts. The sulphonated benzimidazole derivatives contain preferably 2 sulphonic acid groups and one fatty acid radical having approximately from 8 to 22 carbon atoms. Alkylarylsulphonates are, for example, the sodium, calcium or triethanolamine salts of dodecylbenzenesulphonic acid, of dibutylnaphthalenesulphonic acid or of a naphthalenesulphonic acid/formaldehyde condensation product. Also suitable are corresponding phosphates, such as, for example, salts of the phosphoric acid ester of an adduct of p-nonylphenol with from 4 to 14 mols of ethylene oxide.

Suitable nonionic surfactants are especially polyglycol ether derivatives of aliphatic or cycloaliphatic alcohols, of saturated or unsaturated fatty acids and of alkylphenols, that may contain from 3 to 30 glycol ether groups and from 8 to 20 carbon atoms in the (aliphatic) hydrocarbon radical and from 6 to 18 carbon atoms in the alkyl radical of the alkylphenols. Further suitable nonionic surfactants are the water-soluble adducts of polyethylene oxide with polypropylene glycol, ethylenediaminopolypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The said compounds normally contain from 1 to 5 ethylene glycol units per propylene glycol unit.

There may be mentioned as examples of nonionic surfactants nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Also suitable are fatty acid esters of polyoxyethylenesorbitan, such as polyoxyethylenesorbitan trioleate.

Cationic surfactants are especially quaternary ammonium salts that contain, as N-substituent, at least one alkyl radical having from 8 to 22 carbon atoms and, as further substituents, lower unsubstituted or halogenated alkyl, benzyl or lower hydroxyalkyl radicals. These salts are preferably in the form of halides, methyl sulphates or ethyl sulphates, for example stearyltrimethylammonium chloride or benzyldi(2-chloroethyl)ethylammonium bromide.

The surfactants customarily employed in the art of formulation are described, inter alia, in the following publications:

"McCutcheon's Detergents and Emulsifiers Annual" MC Publishing Corp., Ridgewood, N.J. 1979; Dr. Helmut Stache, "Tensid-Taschenbuch", Carl Hanser Verlag, Munich/Vienna 1981.

The pesticidal preparations generally contain—based on weight—from 0.1 to 99%, especially from 0.1 to 95%, active ingredient of the formula I or combinations thereof with other insecticides or acaricides, from 1 to 99.9% solid or liquid adjuvant and from 0 to 25%, especially from 0.1 to 20%, surfactant. Whereas commercial products will preferably be formulated as concentrates, the end user will normally employ dilute formulations, which contain considerably lower concentrations of active ingredient.

The compositions may also contain further adjuvants, such as stabilisers, anti-foams, viscosity regulators, binders, tackifiers and fertilisers, or other active ingredients for achieving specific effects.

Example 1: Manufacture of (3-phenoxy-4-fluorobenzyl) (2,2-dichloro-3,3-dimethylcyclooropylmethyl) ether 2.2 g of 2,2-dichloro-3,3-dimethylcyclopropylmethanol and 3.2 g of 3-phenoxy-4-fluorobenzyl bromide dissolved in 20 ml of a mixture of toluene and dimethylformamide (1/1) are added dropwise while cooling with ice (0°–5° C.), under a nitrogen atmosphere, to 0.6 g of sodium hydride (50% dispersion in mineral oil) in 50 ml of toluene/dimethylformamide (1/1). When the reaction has subsided, the whole is stirred for 16 hours at room temperature to complete the reaction, poured onto saturated ammonium chloride solution and extracted with toluene. The combined toluene extracts are washed with saturated sodium chloride solution, dried over MgSO$_4$ and concentrated in a rotary evaporator. The resulting crude product is chromatographed on silica gel using hexane/toluene (1:1). The title compound of the formula

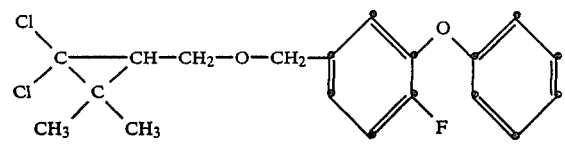

is obtained in the form of a clear oil having a refractive index $n_D^{24} = 1.5488$ (compound no. 1).

The following compounds of the formula I are also obtained as described above:

| Compound no. | $X_1$ | $X_2$ | $R_1$ | $R_2$ | Physical data |
|---|---|---|---|---|---|
| 2 | Cl | Cl | H | Br | $n_D^{22} = 1.5759$ |
| 3 | Cl | Cl | H | Cl | $n_D^{22} = 1.5680$ |
| 4 | Cl | Cl | H | H | $n_D^{24} = 1.5524$ |
| 5 | Cl | Cl | H | F | $n_D^{25} = 1.5400$ |
| 6 | F | F | H | F | $n_D^{21} = 1.5178$ |
| 7 | Br | Cl | H | H | $n_D^{23} = 1.5572$ |
| 8 | Br | Br | H | H | $n_D^{22} = 1.5725$ |
| 9 | Br | Br | H | F | $n_D^{22} = 1.5662$ |
| 10 | Br | Cl | H | F | $n_D^{22} = 1.5438$ |
| 11 | Br | Cl | F | H | $n_D^{22} = 1.5452$ |
| 12 | Fl | Cl | F | H | $n_D^{22} = 1.5275$ |
| 13 | F | Cl | H | F | $n_D^{22} = 1.5219$ |
| 14 | Br | Br | F | H | $n_D^{22} = 1.5608$ |
| 15 | F | Cl | H | H | $n_D^{22} = 1.5360$ |
| 16 | F | F | F | H | $n_D^{22} = 1.5200$ |
| 17 | F | F | H | H | $n_D^{21} = 1.5208$ |
| 18 | Cl | Cl | F | Cl | $n_D^{22} = 1.5381$ |
| 19 | Cl | Cl | F | $CH_3$ | $n_D^{24} = 1.5365$ |
| 20 | Cl | Cl | F | F | $n_D^{24} = 1.5362$ |
| 21 | F | Cl | H | $-OCH_3$ | $n_D^{25} = 1.5444$ |
| 22 | Br | Br | H | $-OCH_3$ | $n_D^{25} = 1.5759$ |
| 23 | F | F | F | F | $n_D^{25} = 1.5082$ |
| 24 | Cl | Cl | F | $-CH_3$ | $n_D^{24} = 1.5365$ |
| 25 | Cl | Cl | H | $-OCH_3$ | $n_D^{25} = 1.5498$ |

The following compounds of the formula I can also be obtained as described in Example 1:

| $X_1$ | $X_2$ | $R_1$ | $R_2$ |
|---|---|---|---|
| F | Cl | H | $CF_3$ |
| F | Br | H | Cl |

EXAMPLE 2: Formulations for liquid active ingredients of the formula I according to Example 1 or combinations of those active ingredients with other insecticides or acaricides (%=percent by weight)

| 2.1 Emulsifiable concentrates | (a) | (b) | (c) |
|---|---|---|---|
| active ingredient or active ingredient combination | 25% | 40% | 50% |
| Ca dodecylbenzenesulphonate | 5% | 8% | 6% |
| castor oil polyethylene glycol ether (36 mol EO) | 5% | — | — |
| tributylphenolpolyethylene glycol ether (30 mol EO) | — | 12% | 4% |
| cyclohexanone | — | 15% | 20% |
| xylene mixture | 65% | 25% | 20% |

Emulsions of any desired concentration can be produced from such concentrates by dilution with water.

| 2.2 Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol MW 400 | — | 70% | — | — |
| N—methyl-2-pyrrolidone | — | 20% | — | — |
| epoxidised coconut oil | — | — | 1% | 5% |
| petroleum fraction (boiling range 160–190° C.) | — | — | 94% | — |

The solutions are situated for use in the form of very small drops.

| 2.3 Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient is dissolved in methylene chloride and sprayed onto the carrier, and the solvent is then evaporated off in vacuo.

| 2.4 Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready-for-use dusts are obtained by mixing the carriers intimately with the active ingredient.

Formulations for solid active ingredients of the formula I according to Example 1 or combinations of those active ingredients with other insecticides or acaricides (%=percent by weight):

| 2.5 Wettable powders | (a) | (b) | (c) |
|---|---|---|---|
| active ingredient or active ingredient combination | 25% | 50% | 75% |
| Na lignosulphonate | 5% | 5% | — |
| Na lauryl sulphate | 3% | — | 5% |
| Na diisobutylnaphthalene-sulphonate | — | 6% | 10% |
| octylphenol polyethylene glycol ether (7–8 mol EO) | — | 2% | — |
| highly dispersed silicic acid | 5% | 10% | 10% |
| kaolin | 62% | 27% | — |

The active ingredient or the active ingredient combination is mixed with the adjuvants and ground well in a suitable mill.

Wettable powders are obtained that can be diluted with water to form suspensions of any desired concentration.

| 2.6 Emulsifiable concentrate | |
|---|---|
| active ingredient or active ingredient combination | 10% |
| octylphenol polyethylene glycol ether (4–5 mol EO) | 3% |
| Ca dodecylbenzenesulphonate | 3% |
| castor oil polyglycol ether (36 mol EO) | 4% |

-continued

| 2.6 Emulsifiable concentrate | |
|---|---|
| cyclohexanone | 30% |
| xylene mixture | 50% |

Emulsions of any desired concentration can be prepared from this concentrate by dilution with water.

| 2.7 Dusts | (a) | (b) |
|---|---|---|
| active ingredient or active ingredient combination | 5% | 8% |
| talcum | 95% | — |
| kaolin | — | 92% |

Ready-for-use dusts are obtained by mixing the active ingredient with the carrier and grinding the mixture in a suitable mill.

| 2.8 Extruder granulate | |
|---|---|
| active ingredient or active ingredient combination | 10% |
| Na lignosulphonate | 2% |
| carboxymethylcellulose | 1% |
| kaolin | 87% |

The active ingredient or the active ingredient combination is mixed and ground with the adjuvants and moistened with water. The mixture is extruded, granulated and then dried in a stream of air.

| 2.9 Coated granulate | |
|---|---|
| active ingredient or active ingredient combination | 3% |
| polyethylene glycol (MW 200) | 3% |
| kaolin | 94% |

The finely ground active ingredient or the active ingredient combination is applied uniformly, in a mixer, to the kaolin, which has been moistened with polyethylene glycol. Dust-free coated granulates are thus obtained.

| 2.10 Suspension concentrate | |
|---|---|
| active ingredient or active ingredient combination | 40% |
| ethylene glycol | 10% |
| nonylphenol polyethylene glycol ether (15 mol EO) | 6% |
| Na lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active ingredient combination is intimately mixed with the adjuvants. A suspension concentrate is thus obtained from which suspensions of any desired concentration can be produced by dilution with water.

Example 3: Action against *Lucilia sericata (larvae)*

1 ml of an aqueous preparation containing 0.5% active ingredient is added at 50° C. to 9 ml of a culture medium. Approximately 30 *Lucilia sericata* larvae which have just emerged are then added to the culture medium. The insecticidal action is assessed after 48 and 96 hours by determining the mortality.

In this test, compounds of the formula I according to Example 1 exhibit good action against *Lucilia sericata*.

Example 4: Contact action against *Aphis craccivora*

Approximately 200 individuals of the species *Aphis craccivora* are settled, before the start of the test, on 4- to 5-day-old bean seedlings (*Vicia faba*) which have been grown in pots. After 24 hours, an aqueous preparation containing 400 ppm of the compound to be tested is sprayed directly onto the plants so treated until they are thoroughly wetted. Two plants are used per test compound. The mortality achieved is evaluated after a further 24 and 72 hours. The test is carried out at 21°–22° C. and at a relative humidity of approximately 55%.

Compounds nos. 1, 2, 4 and 5 according to Example 1 exhibit 80–100% action in this test.

Example 5: Contact action against *Myzus persicae*

Approximately 200 individuals of the species *Myzus persicae* are settled, before the start of the test, on approximately 4- to 5-day-old bean seedlings (*Vicia faba*) which have been grown in water. After 24 hours, an aqueous suspension containing up to 200 ppm of the compound to be tested is sprayed directly onto the plants so treated until they are thoroughly wetted. Two plants are used per test substance. The mortality achieved is evaluated 24 and 72 hours after application. The test is carried out at 21°–22° C. and at approximately 60% relative humidity.

Compounds according to Example 1 exhibit good action in this test.

Example 6: Contact action against *Laodelphax striatellus* and *Nilaparvata lugens* (nymphs)

The test is carried out on growing plants. In each case, eight rice plants (thickness of the stalk 4 mm) approximately 20 cm tall are planted in pots (diameter 8 cm).

The plants, which are located on a turntable, are sprayed with 100 ml of an aqueous preparation containing 400 ppm of the formulated active inqredient. After the spray coating has dried, 20 nymphs of the test insect in the third stage of development are settled on each plant. In order to prevent the cicadas from escaping, a glass cylinder which is open at both ends is placed over each of the infested plants and covered with a gauze lid. The nymphs are kept on the treated plants for 6 days until they have reached the adult stage. The test is evaluated for % mortality 6 days after the treatment.

Compound no. 1 according to Example 1 exhibits 80–100% action against *Nilaparvata lugens* in this test.

Example 7: Systemic action against *Nilaparvata lugens*

Approximately 10-day-old rice plants (approximately 10 cm tall) and a plastics beaker containing 150 ml of an aqueous emulsion preparation of the active ingredient to be tested in a concentration of 100 ppm are used. The beaker is closed by a plastics lid provided with holes. The root of each rice plant is pushed through a hole in the plastics lid into the aqueous test preparation. The hole is then packed with cotton wool in order to hold the plant in position. 20 *Nilafarvata lugens* nymphs in the N2 to N3 stage are then settled on the rice plants, and the plants are covered with a plastics cylinder. The test is carried out at 26° C. and 60% relative humidity, with an illumination period of 16 hours. After 6 days, the number of dead test insects is estimated in comparison with untreated controls. It is thus determined whether the active ingredient taken up via the roots kills the test insects on the upper parts of the plant.

Compound no. 1 according to Example 1 exhibits 80–100% action (mortlity) against *Nilaparvata lugens* in the above test.

Example 8: Action as a stomach insecticide

Cotton plants that are approximately 25 cm tall and are planted in pots are sprayed with aqueous active ingredient emulsions that contain the active ingredient in a concentration of 400 ppm.

When the spray coating has dried, Soodootera *littoralis* or *Heliothis virescens* larvae in the first larval stage are settled on the cotton plants. The test is carried out at 24° C. and approximately 60% relative humidity. The % mortality of the test insects compared with untreated controls is determined after 120 hours.

Compound no. 1 according to Example 1 exhibits 80–100% action against Spodoptera larvae in this test.

Example 9: Action against *Nephotettix cincticeps* (nymphs)

The test is carried out on growing plants. Approximately 20-day-old rice plants approximately 15 cm tall are planted in pots (diameter 5.5 cm).

The plants, which are located on a turntable, are each sprayed with 100 ml of an aqueous active ingredient emulsion containing 400 ppm of the active ingredient to be tested. After the spray coating has dried, 20 nymphs of the test insect in the second or third stage of development are settled on each plant. In order to prevent the cicadas from escaping, a Plexiglass cylinder is placed over each infested plant and covered with a gauze lid. The nymphs are kept on the treated plants for 6 days. The test is carried out at a temperature of approximately 26° C., at 55% relative humidity and with an illumination period of 16 hours.

The compounds according to the invention according to Example 1 exhibit good action in this test.

Example 10: Action against soil insects (*Diabrotica balteata*)

Five corn seedlings 1–3 cm in length and a circle of filter paper are immersed in an aqueous active ingredient solution containing approximately 4% by volume of acetone. The content of active ingredient in the solution used is 400 ppm. The immersed circle of filter paper is placed on the bottom of a plastics beaker (capacity 200 ml), and a dry circle of filter paper, the corn seedlings and 10 *Diabrotica balteata* larvae in the second or third larval stage are placed thereon. The arrangement is kept in daylight at approximately 24° C. and 40–60% relative humidity. The test is assessed after 6 days in comparison with untreated control arrangements.

Compounds nos. 1 and 4 according to the invention exhibit an action of 80–100% (mortality) in this test.

Example 11: Action against animal-parasitic mites

Batches comprising approximately 50 mites in various stages of development (mixed population: larvae, nymphs and adults) are removed from hens infested with *Dermanyssus gallinae*. The batches of mites are wetted with an aqueous emulsion, suspension or solution containing 400 ppm of the active ingredient to be tested. To that end, the liquid preparation containing the active ingredient is poured over the batches of mites in a test tube; the liquid is then soaked up with a swab.

The mites thus wetted and treated are left in the test tube for 72 hours. The mortality of the treated mites compared with untreated control batches is then determined.

Compound no. 1 according to the above Example 1 exhibits 100% action in the above test.°

Example 12: Action against ticks: killing action in various stages of development The test objects used per batch are not replete larvae (in each case approximately 50), nymphs (in each case 5) or adults (in each case 5) of the tick species *Rhipicephalus bursa, Amblyomma hebraeum* and *Boophilus microplus.* The test animals (in the given number are immersed for a short time in a test tube containing from 2 to 3 ml of an aqueous emulsion of the compound to be investigated in a concentration of 400 ppm. The test tubes are then closed with a cotton wool plug and shaken 10 minutes after the immersion of the test animals. The active ingredient emulsion is soaked up by the cotton wool plugs and the wetted test animals are left in the test tubes thus contaminated. The test is evaluated (% mortality) after 3 days in the case of larvae and after 14 days in the case of nymphs and adults.

Compound no. 1 according to the above Example 1 exhibits 100% action (mortality) against nymphs and adults of *Amblyomma hebraeum* in the above test.

Example 13: Action against *Piricularia oryzae* on rice plants—residual protective action (a) After 2 weeks' cultivation, rice plants are sprayed with an aqueous spray formulation (containing 200 ppm of active ingredient) prepared from a wettable powder of the active ingredient. After 48 hours, the treated plants are infected with a conidia suspension of the fungus.

After 5 days' incubation at 95–100% relative humidity and at 24° C., the fungal attack is evaluated.

(b) Systemic action: A spray formulation prepared from a wettable powder of the active ingredient is poured onto 2-week-old rice plants which are in pots (0.006% relative to the volume of earth). The pots are then filled with water until the lower parts of the stalks of the rice plants are submerged. After 96 hours, the treated rice plants are infected with a conidia suspension of the fungus. After the infected plants have been incubated for 5 days at 95–100% relative humidity and at approximately 24° C., the fungal attack is evaluated.

Rice plants treated with a spray formulation containing as active ingredient a compound of the formula I according to Example 1 exhibit only slight fungal attack compared with untreated control plants (100% attack). For example, compound no. 1 reduces fungal attack in the above test (a) to approximately 20%.

We claim:

1. A compound of the formula I

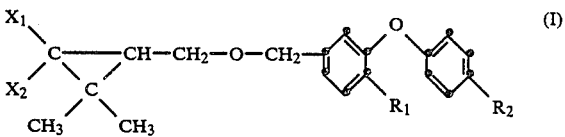

in which $X_1$ and $X_2$ each independently of the other represents fluorine, chlorine or bromine;

$R_1$ represents hydrogen or fluorine; and $R_2$ represents hydrogen, fluorine, chlorine, bromine, methyl, trifluoromethyl or methoxy, and, if $X_1$ and $X_2$ have different meanings, the optical isomers of the compound of the formula I.

2. A compound according to claim 1 of the formula I, characterised in that $X_1$ and $X_2$ represent chlorine;

$R_1$ represents hydrogen or fluorine; and $R_2$ represents hydrogen, fluorine, chlorine or bromine.

3. A compound according to claim 2 of the formula

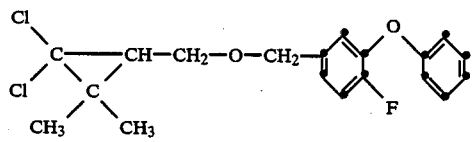

4. A compound according to claim 2 of the formula

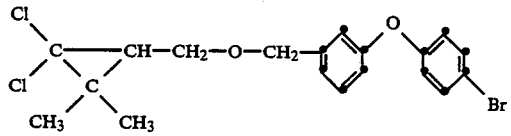

5. A compound according to claim 1 of the formula

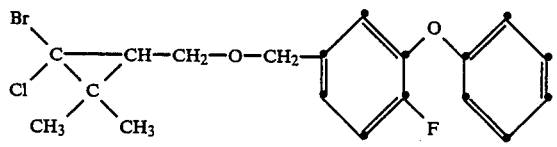

6. A compound according to claim 2 of the formula

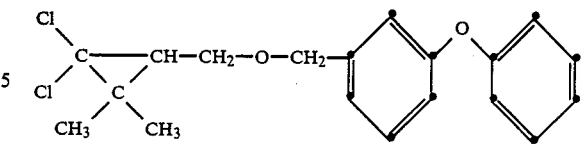

7. A compound according to claim 1 of the formula

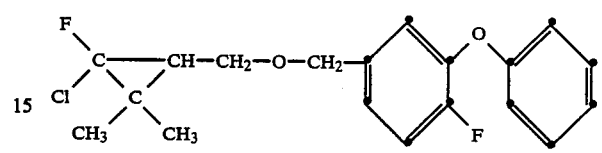

8. A pesticidal composition containing as active component a compound according to claim 1 together with suitable carriers and/or other adjuvats.

9. A method for controlling insects and representatives of the other Acarina, characterised in that the pests or their various stages of development and/or their habitat is/are brought into contact or treated with a pesticidally effective amount of a compound of the formula I according to claim 1 or with a composition containing a pesticidally effective amount of that compound together with adjuvants and carriers.

10. The method according to claim 9 for controlling insects that damage plants.

11. The method according to claim 10 for controlling insects that damage plants in rice crops.

12. A method for controlling fungi that damage plants, characterised in that the fungi or their spores or the location attacked by them is/are brought into contact or treated with a fungicidally effective amount of a compound of the formula I according to claim 1 or with a composition containing a fungicidally effective amount of that compound together with adjuvants and carriers.

13. The method according to claim 12 for controlling fungi that damage plants in rice crops.

* * * * *